United States Patent [19]

Itoh et al.

[11] Patent Number: 5,322,760
[45] Date of Patent: Jun. 21, 1994

[54] NONLINEAR OPTICAL ELEMENT

[75] Inventors: Yuzo Itoh, Hitachi; Atsushi Kakuta, Hitachiota; Akio Mukoh, Mito, all of Japan

[73] Assignee: Hitachi, Ltd., Tokyo, Japan

[21] Appl. No.: 800,427

[22] Filed: Nov. 29, 1991

[30] Foreign Application Priority Data

Nov. 30, 1990 [JP] Japan .................. 2-329078
Jul. 31, 1991 [JP] Japan .................. 3-191931

[51] Int. Cl.$^5$ .................................................. G03C 1/76
[52] U.S. Cl. ................................ 430/270; 540/123; 540/124; 540/125; 540/126; 540/127; 540/128; 540/139
[58] Field of Search ............... 540/123, 124, 125, 126, 540/127, 128, 139; 430/270

[56] References Cited

U.S. PATENT DOCUMENTS

| | | | |
|---|---|---|---|
| 4,622,179 | 11/1986 | Eda | 540/139 |
| 4,854,676 | 8/1989 | Kalyanaraman et al. | 350/354 |

FOREIGN PATENT DOCUMENTS

| | | |
|---|---|---|
| 0191970 | 8/1986 | European Pat. Off. |
| 0198140 | 10/1986 | European Pat. Off. |
| 0279426 | 8/1988 | European Pat. Off. |
| 0313943 | 3/1989 | European Pat. Off. |
| 0344891 | 12/1989 | European Pat. Off. |
| 0356971 | 7/1990 | European Pat. Off. |
| 0381211 | 8/1990 | European Pat. Off. |
| 0418611 | 3/1991 | European Pat. Off. |

*Primary Examiner*—Thurman K. Page
*Assistant Examiner*—Jyothsna Venkat
*Attorney, Agent, or Firm*—Antonelli, Terry, Stout & Kraus

[57] ABSTRACT

A nonlinear optical element comprising a tetraazaporphyrin compound represented by the formula (I):

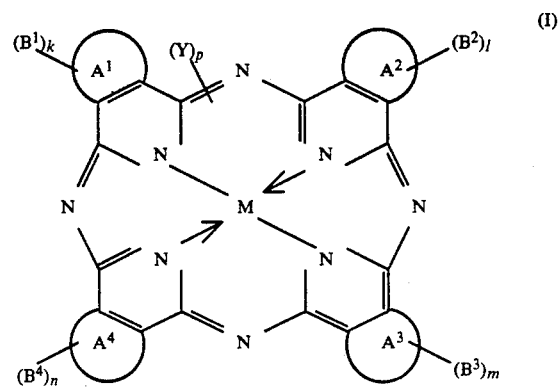

This nonlinear optical element is excellent in that it is improved over low switching speed of the conventional inorganic materials and over small nonlinearity and poor chemical and physical stability and workability of the conventional organic materials.

6 Claims, 2 Drawing Sheets

F I G. 1
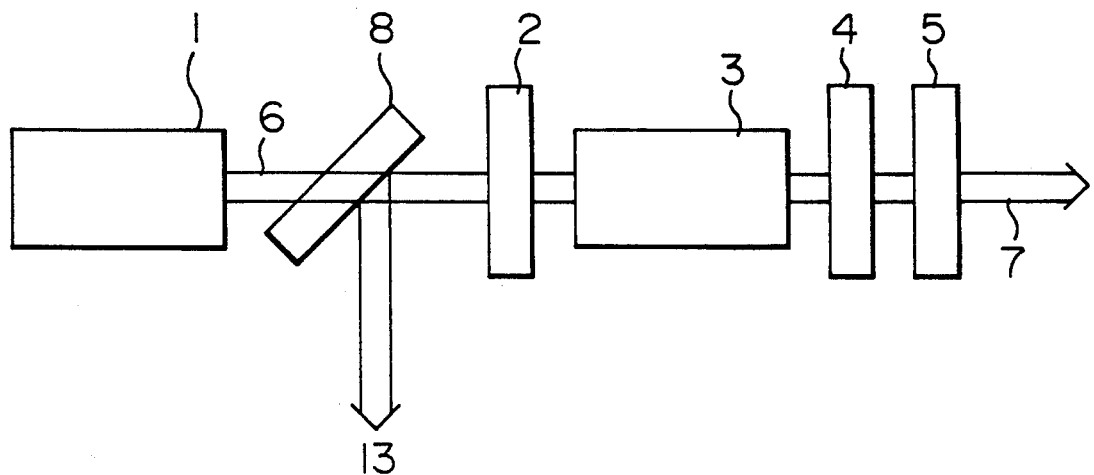
F I G. 2
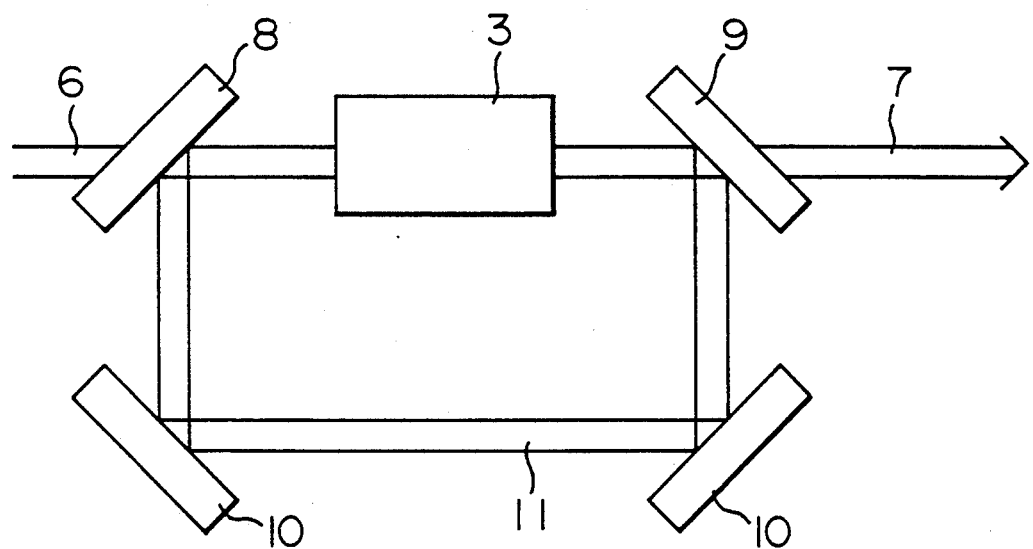

NONLINEAR OPTICAL ELEMENT

This invention relates to a nonlinear optical element using an organic nonlinear optical material.

Recently, nonlinear optical materials having the characteristic that optical output makes nonlinear response to the intensity of optical input are used in the optical high-speed operation elements or parallel operation elements specifically designed for generation of optical higher harmonics or elevation of operation speed. Among the presently known nonlinear optical materials are, for instance, $LiNbO_3$ and KDP which are inorganic materials and p-nitrodimethylaminobenzene, polydiacetylene and chalcone derivatives which are organic materials.

However, the inorganic nonlinear optical materials generally have the defect that the harmonic generation efficiency is low because of their low nonlinear susceptivity, so that when these materials are used for operation elements, there can not be obtained a satisfactory characteristics. On the other hand, in the case of the organic nonlinear optical materials, although high in nonlinear susceptivity as compared with the inorganic materials, they are low in chemical stability against oxidation or decomposition, posing the problems in practical use of these materials.

Said conventional nonlinear optical materials had typically the problem of low switching speed in the case of the inorganic materials and the problems of small nonlinearity in the case of third-order effect and poor chemical and physical stability and workability in the case of the organic materials. The object of the present invention, therefore, is to provide an excellent nonlinear optical material which is freed of said prior art problems.

The present invention relates to a nonlinear optical element using a tetraazaporphyrin compound represented by the formula (I):

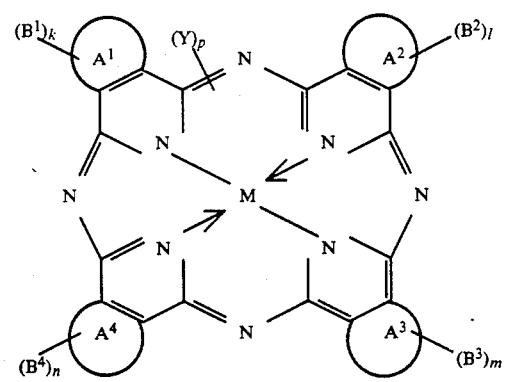

wherein M represents any of the metals of Groups Ia, Ib, IIa, IIb, IIIa, IVa, IVb, Va, Vb, VIa, VIb, VIIa and VIII in the Periodic Table, Si and Ge; Y represents any of the monovalent organic groups, hydroxyl groups and halogen atoms which can be bonded to M; p is an integer of 0–2, and when p is 2, Y's may be the same or different from each other; $A^1$, $A^2$, $A^3$ and $A^4$ each represents an aromatic ring or heterocyclic ring, but all of $A^1$, $A^2$, $A^3$ and $A^4$ can not be a benzene ring at the same time; $B^1$, $B^2$, $B^3$ and $B^4$ may be the same or different from each other and each represents a monovalent organic group, halogen atom or hydrogen atom, but all of $B^1$, $B^2$, $B^3$ and $B^4$ can not be hydrogen atom at the same time; and k, l, m and n represent independently an integer of 0–4, but $k+l+m+n \geq 1$.

In the accompanying drawings:

FIG. 1 is a schematic illustration of an example of nonlinear optical element according to the present invention.

FIG. 2 is a schematic illustration of another example of nonlinear optical element according to the present invention.

Figure 3:
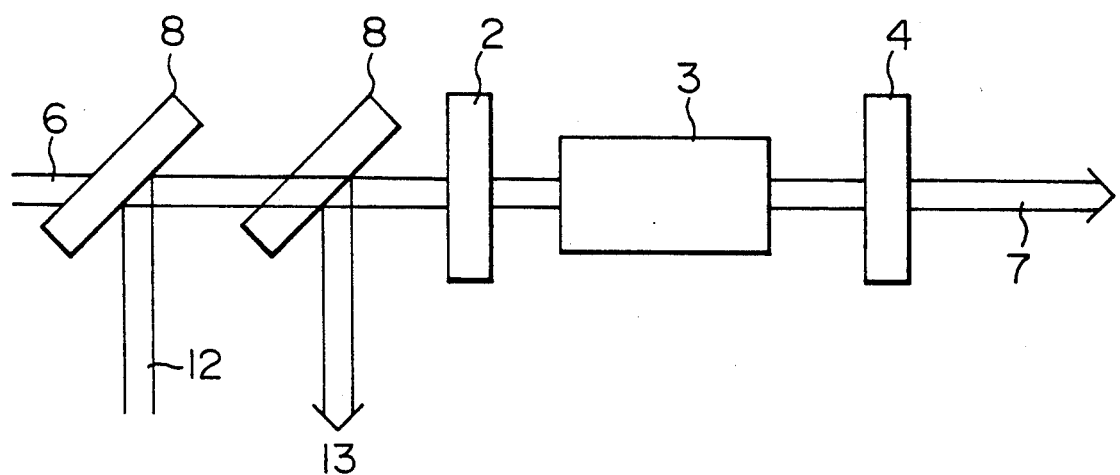
FIG. 3 is a schematic illustration of still another example of nonlinear optical element according to the present invention.

In the drawings throughout, like reference numerals are used to indicate like elements, and wherein:
1: light source for actuating the element
2, 4: semitransparent mirror adapted to the element structure
3: samples of tetraazaporphyrin compound of this invention
5: polarizing plate
6: output light from light source
7: output light which has undergone a change by the element of this invention
8, 9: semitransparent mirror adapted to the element structure
10: reflecting mirror
11: half-transmitted light and light returned by reflecting mirror
12: another form of light source
13: reflected light from half-transmitted mirror The tetraazaporphyrin compounds represented by the formula (I) are soluble in aromatic, halogen-type, ketone-type, ether-type, alcohol-type, ester-type, formamide-type, sulfoxide-type and saturated hydrocarbon solvents as well as in liquid organic acids and mineral acids, so that said compounds can be easily purified with these solvents or acids to a high-degree of purity. The nonlinear optical materials are required to have high transparency at the practically used wavelength and good crystal quality, so that it is necessary to prepare a material with high purity. The tetraazaporphyrin compounds of this invention can well meet this requirement.

Examples of the aromatic solvents usable for said purpose in this invention include benzene, toluene, xylene, chlorobenzene, dichlorobenzene, bromobenzene, trimethylbenzene, ethylbenzene, 1-chloronaphthaline, quinoline, aniline and nitrobenzene. Examples of the halogen type solvents include methylene chloride, chloroform, carbon tetrachloride, trichloroethane, dichloroethane and dibromoethane. Examples of the ether type solvents are diethyl ether, dibutyl ether, tetrahydrofuran, ethylene glycol monomethyl ether, ethylene glycol dimethyl ether, diethylene glycol monomethyl ether and diethylene glycol dimethyl ether. The alcohol-type solvents include methanol, ethanol, isopropyl alcohol, butanol, benzyl alcohol, ethylene glycol and cyclohexanol. Examples of the ester-type solvents are methyl acetate, ethyl acetate, propyl acetate, butyl acetate, cyclohexyl acetate, methyl propionate, ethyl propionate, propyl propionate, methyl butyrate and ethyl butyrate. The formamide type solvents include N-methylformamide, dimethylformamide, diethylformamide, etc., and the sulfoxide type solvents include dimethyl sulfoxide, etc. Examples of the ketone type solvents are acetone, methyl methyl ketone, methyl propyl ketone, cyclopentanone, cyclohexanone and acetone alcohol, and acetone alcohol, and examples of the saturated hydrocarbon solvents include hexane, heptane, octane, nonane, decane, undecane, dodecane, cyclohexane, methylcyclohexane, ethylcyclohexane, cycloheptane, cyclooctane and decalin. Examples of the organic acids usable for said purpose in this invention include acetic acid, propionic acid, butyric acid, formic acid, etc., and examples of the inorganic acids include concentrated nitric acid, concentrated sulfuric acid, etc. It is to be noted that the above-mentioned are merely examples of the solvents and acid usable for said purpose in this invention.

Referring to the formula (I), M in this formula can be, for example, Mg, Ba, Ca, Sr, Zn, Cd, Al, Ga, In, Tl, Ti, Zr, Si, Ce, Sn, Pb, V, Ta, As, Sb, Bi, Cr, Mo, W, Se, Te, Fe, Co, Ni or Pd, Y in the formula (I) represents a monovalent organic group, a halogen atom or a hydroxyl group. Exemplary of the monovalent organic groups represented by Y are alkyl, aryl, aralkyl, ester, alkoxyl, aryloxy, trialkylsiloxyl, triarylsiloxyl, triaryloxysiloxy, acyloxyl, alkylthio, arylthio, alkylsulfonyl, arylsulfonyl, carbamoyl and nitrile groups. Examples of the halogen atoms represented by Y are Cl, Br and I. Any of these organic groups may have a substituent. The above-mentioned are merely examples and other groups may be well employed.

As examples of the monovalent organic groups represented by $B^1$, $B^2$, $B^3$ and $B^4$ which can serve as substituents of the aromatic or heterocyclic rings $A^1$, $A^2$, $A^3$ and $A^4$ in the formula (I) there can be mentioned alkyl, aryl, aralkyl, ester, alkoxyl, aryloxy, trialkylsiloxyl, triarylsiloxyl, triaryloxysiloxy, acyloxyl, alkylthio, arylthio, alkylsulfonyl, arylsulfonyl, carbamoyl and nitrile groups. These organic groups may have a substituent. The groups mentioned above are merely examples and should in no way be taken as restrictive.

The type of the substituent Y and the monovalent organic group substituting the aromatic or heterocyclic ring exerts a great influence not only on solubility when a compound of the formula (I) is dissolved in an organic solvent but also on melting point of that compound as well as its crystal structure, optical properties (absorption spectrum, refractive index and anisotropy thereof) and nonlinear optical constant.

In the present invention, the tetraazaporphyrin compounds represented by the formula (I) are preferably those of the formula (I) wherein M is Si, Ge, Ti, V, Mo, Cr, Co or Ni.

It is also desirable that said tetraazaporphyrin compounds are those of the formula (I) where all of k, l, m and n are 1.

The tetraazaporphyrin compounds of this invention are also preferably those of the formula (I) wherein Y is aryloxyl, alkoxyl, trialkylsiloxyl, trialkylsiloxyl, trialkoxysiloxyl, triarylsiloxyl, trityloxyl, acyloxyl, alkyl or aryl group.

It is further desirable that the tetraazaporphyrin compounds of this invention are those in which the aromatic or heterocyclic ring(s) represented by $A^1$, $A^2$, $A^3$ and $A^4$ in the formula (I) is(are) the one(s) selected from the following:

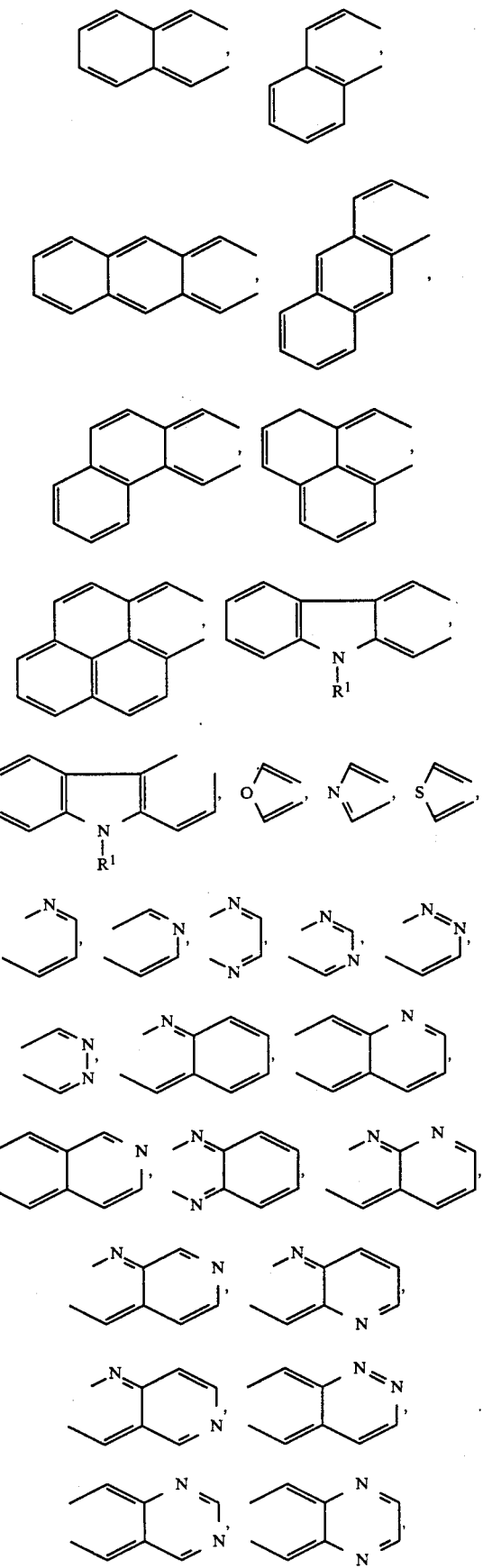

-continued

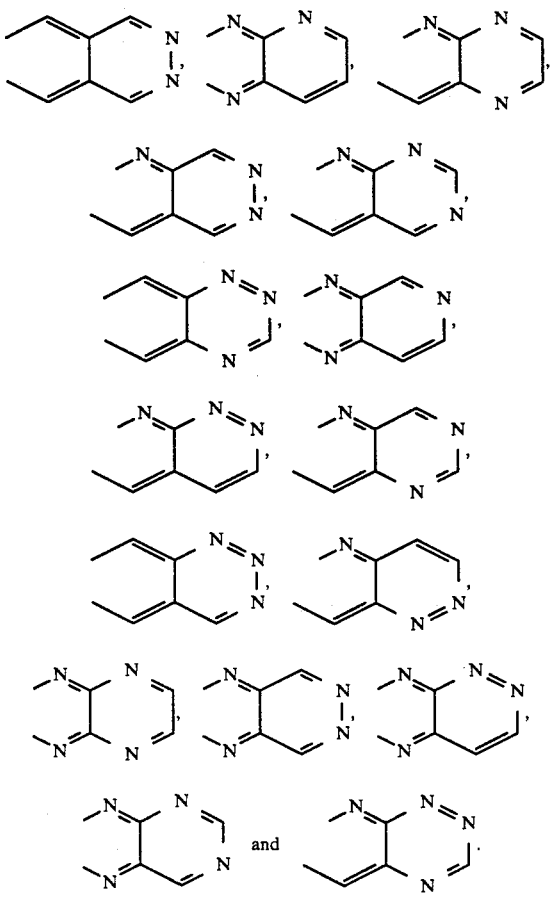

It is desirable that the aromatic or heterocyclic rings represented by $A^1$, $A^2$, $A^3$ and $A^4$ in the formula (I) have at least one organic group selected from the group consisting of the following substituents: $-R^2$, $-OR^3$, $-SiR^4R^5R^6$, $-SO_2NR^7R^8$, $-CO.R^9$, $-COO.R^{10}$, $-OCOR^{11}$, $-CONHR^{12}$, $-NR^{13}R^{14}$, $-SR^{15}$ and $-SO_2R^{16}$ wherein $R^1$ is an alkyl group having 1-3 carbon atoms, and $R^2$ to $R^{16}$ are a hydrogen atom or an alkyl or aryl group which may have a substituent. The methods for the synthesis of these tetrazaporphyrin compounds are described in detail in, for instance, Zhurnal Obshchei Khimii, Vol. 39, page 2,554 (1969), Mol. Cryst. Liq. Cryst., Vol. 112, page 345 (1984) and European Patent No. 344-891-A (189).

The tetraazaporphyrin compounds of the formula (I) can be used as a nonlinear optical material, especially the one characterized by nonlinear susceptibility of odd orders, typically 3rd order. As for use of the tetraazaporphyrin compounds of the formula (I), they can be applied to all of the uses of the known nonlinear optical materials, which include wave changing switches, light-light modulators, light demodulators, light mixers, photo-optical switches, electro-optical switches, light amplifiers, photocommutators, optical phase discriminators, phase conjugate mirrors, light waveguides, and optical logical circuits.

An example of nonlinear optical element of known structure in which the present invention is embodied is schematically illustrated in FIG. 1. The output light 6 from light source 1 is applied through semitransparent mirror 2 to sample 3 of a tetraazaporphyrin compound disclosed in the present invention, and thence the light passes through another semitransparent mirror 4 and polarizing plate 5 to give output light 7. Here, by using the known technique of setting the semitransparent mirrors 2 and 4 at the resonance positions adapted to the light used, it is possible to let the output light effectuate nonlinear response or bistable operation effective for optical operation in correspondence to incident light. It is also possible to perform the similar operation efficiently by utilizing the return light 11 or 13 which has been reflected by the semitransparent mirrors 8, 9 or reflecting mirror 10 as shown in FIG. 1, 2, or 3. It is further possible to perform optical operation by arranging the incident light to be the sum of light beams 6 and 12 and by using one of them as pumping light and the other as probe light as shown in FIG. 3.

For practical application of the nonlinear optical material using a tetraazaporphyrin compound represented by the formula (I), it can be used in the states and forms known in the art. That is, said nonlinear optical material, when used singly, may be in either crystal or amorphous state, and its form may be lumpy, plate-like, fibrous, powdery, filmy, etc. It may be also used in combination with other types of material while taking a form such as mentioned above. Further, the tetraazaporphyrin compounds represented by the formula (I) but having the different chemical structures may be combined with each other or the tetraazaporphyrin compounds of the formula (I) may be combined with different types of materials to form a composition having specific or novel functions. Typical examples of the products obtainable by using said nonlinear optical material include lens, coating material for reflecting mirror, optical waveguides, integrated circuits, optical cables, display elements, optical recording materials and photocatalysts. Needless to say, practical application of the present invention is not limited to said types of products but includes various other types of commercial products. In forming these products, there can be adopted any of the known methods and techniques such as adhesion, fusion, electro-deposition, press bonding, sputtering, MBE method, dyeing, melt extrusion, kneading, press molding, coating with solvent, etc. Other techniques may as well be employed.

It is also possible to use a mixture of the different types of tetraazaporphyrin compounds of the formula (I) or a mixture of a tetraazaporphyrin compound of the formula (I) and other material mixed by a suitable method such as dissolving, dispersion, etc.

As for the "other materials" to be mixed with a tetraazaporphyrin compound of the formula (I), they may be either a solid or half-solid substance, and as examples of such other materials usable in this invention, there can be mentioned the following, as inorganic materials: glass, diamond, crystal, silicon dioxide, mica, marble, calcite, single-crystal or amorphous silicon, GaP, GaAs, CdS, dipotassium hydrogenphosphate, lithium niobate, potassium bromide, Rochelle salt, copper sulfate, calcium fluoride, graphite, $SnO_2$, barium titanate, red prussiate, pottery, ceramics, bentonite, cement, metals and alloys thereof, etc., and as organic materials: polycarbonate resin, polysulfone resin, polyarylate resin, polyester resin, polyamide resin, polyimide resin, polysiloxane resin, polyethylene terephthalate resin, polyvinyl acetate resin, polyethylene resin, polypropylene resin, acrylic resin, polybutadiene resin, polyvinyl chloride, vinylidene chloride resin, petroleum resin, melamine resin, epoxy resin, phenol resin, isoprene rubber, ethylene-propylene rubber, norbornene resin, cyanoacrylate resin, styrene resin, copolymers of these resins, paper, cellulose, starch, polysaccharides such as chitin and lignine, collagen, glue, gelatin, agar, silk yarn, cotton yarn, nylon yarn, albumin, globulin, other proteins, woodmeal, bone meal, etc. As low-molecular organic materials, there can be mentioned condensed aliphatic substances such as naphthalene and anthracene, dyes, pigments, urea, tartaric acid, optically active amino-acids, etc. The above-mentioned are merely examples and in no way intended to be limitative to the materials usable in this invention.

In case of using a tetraazaporphyrin compound of the formula (I) by rendering it into a crystal state, there can be used a known method for crystal formation. It is suggested to employ, for example, Bridgman's method, temperature dropping method, solvent evaporation method or solvent composition changing method. Other methods are also usable.

The products formed by using the tetraazaporphyrin compounds of the formula (I) may be subjected to after-treatments for improving appearance or properties, elongating the service life and for other purposes. Such after-treatments include heat annealing, exposure to radiation, electron ray irradiation, light irradiation, application of electric waves, application of magnetic flux and application of ultrasonic waves. Other treatments can be applied as well.

Shown below are the typical examples of chemical structures of the compounds according to the present invention. In the structural formulae shown below, Ph represents phenyl group.

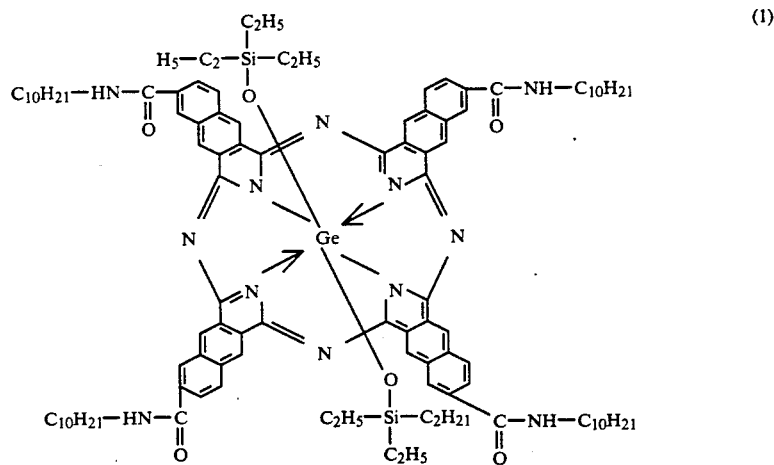

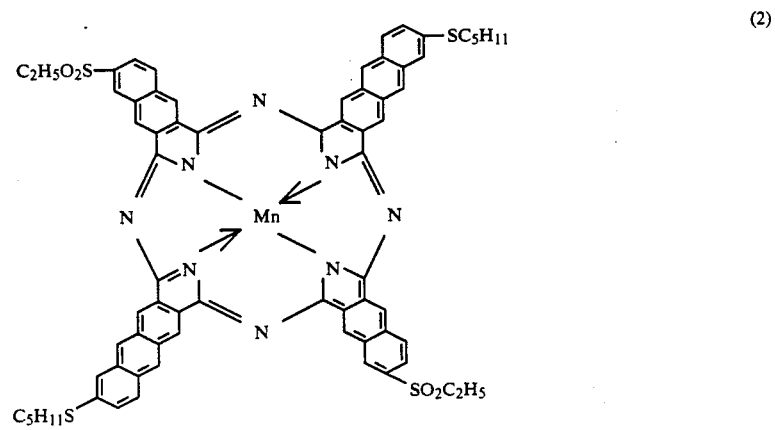

-continued
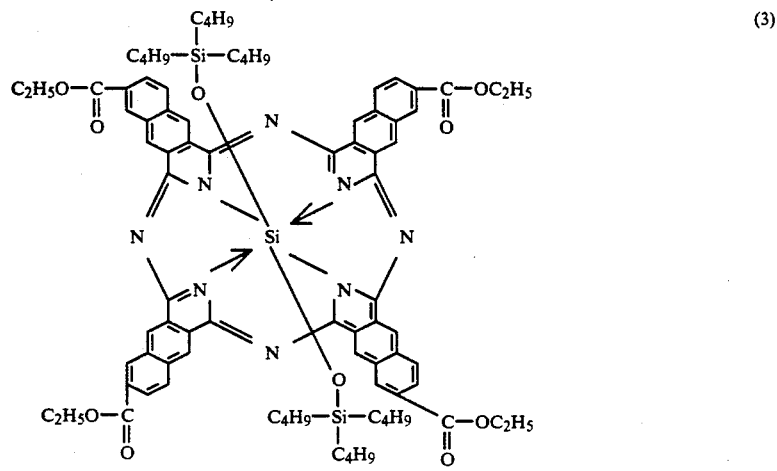
(3)
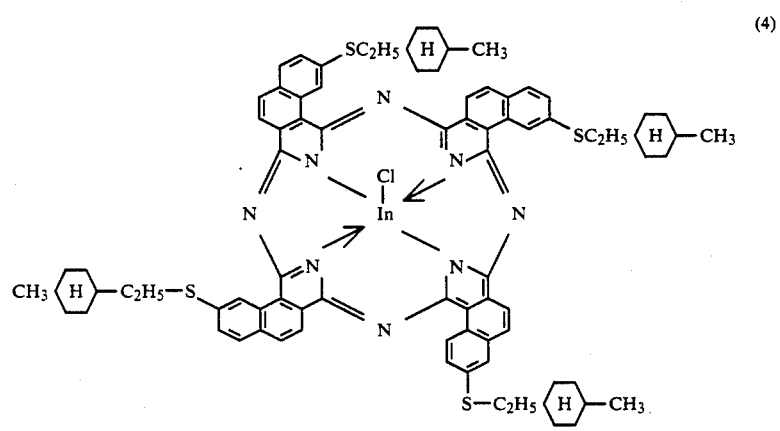
(4)
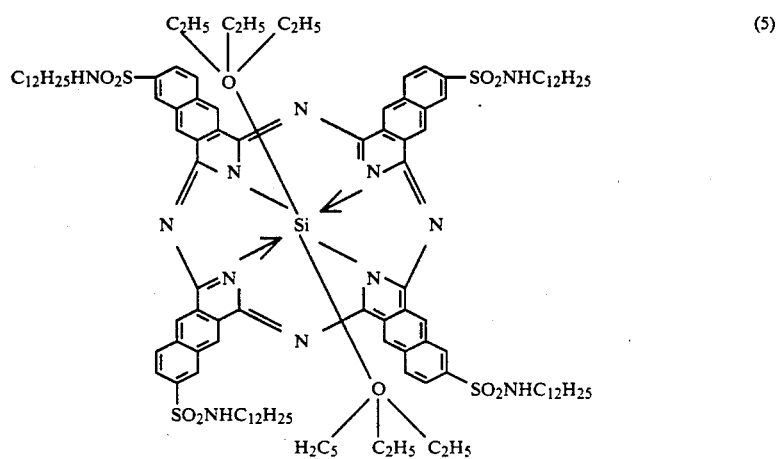
(5)

-continued
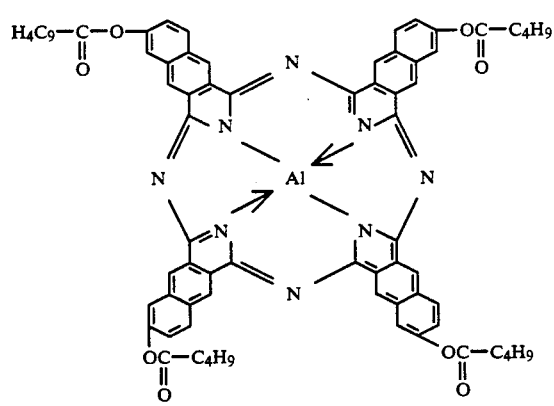
(6)
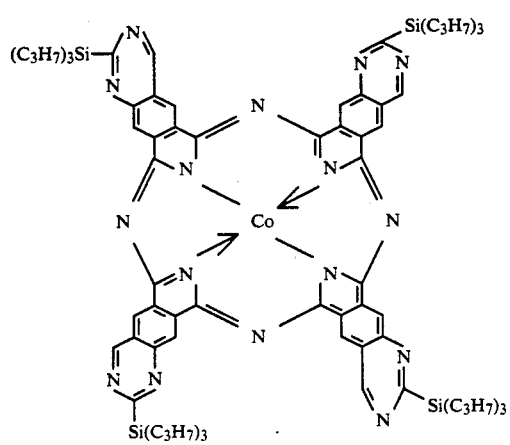
(7)
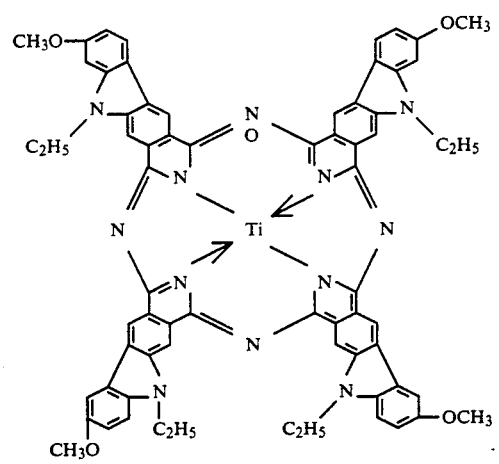
(8)
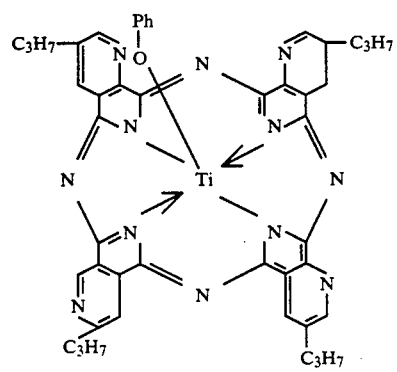
(9)

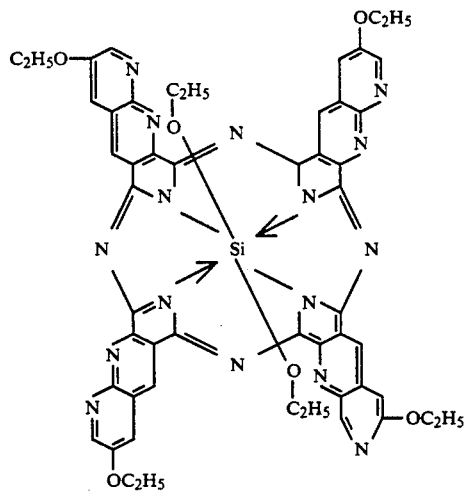

(10)

In the tetraazaporphyrin derivatives of the formula (I) according to the present invention, many conjugated systems are present in the central skeleton, and the nearby electrons are allowed to move easily in the conjugated systems with variation of photo-electric field. Also, since mobility is not the same throughout the whole of conjugated systems, nonlinearity of dipole moment is enlarged and, as a result, massive nonlinear optical response is observed.

EXAMPLE 1

There were prepared the specimens by holding fine powder (particle size being less than 10 μm) of each of the tetraazaporphyrin compounds of this invention specified in Table 1 between a pair of glass plates and a specimen by holding powder of bis(1,2-toluene-sulfonic acid)-2,4-hexadiyne (PTS) between a pair of glass plates. Light with a wavelength of 1,950 nm, obtained by Raman-shifting Nd:YAG laser wavelength, was applied to each of said specimens and luminous intensity of the light of 650 nm, which is the third-order harmonic, was measured. The ratio of luminous intensity of the third-order harmonic of each of the specimens in the embodiment f this invention to that of PTS is shown in Table 1.

TABLE 1

| Specimen | Intensity of third harmonic measured by powder method (ratio ot PTS) |
|---|---|
| Compound of formula (1) | 0.98 |
| Compound of formula (3) | 0.67 |
| Compound of formula (5) | 0.54 |

EXAMPLE 2

Specimens were prepared in the same way as Example 1 by using the tetraazaporphyrin compounds of this invention specified in Table 2, and luminous intensity was measured for each of the specimens in the same way as Example 1 except that irradiation light was changed to YAG: pigment laser light with a wavelength of 1,610 nm. The ratio of luminous intensity of the third-order harmonic of each of said specimens to that of PTS is shown in Table 2.

TABLE 2

| Specimen | Intensity of third harmonic measured by powder method (ratio ot PTS) |
|---|---|
| Compound of formula (8) | 0.38 |
| Compound of formula (10) | 1.02 |

The tetraazaporphyrin derivatives of this invention have a chemically stable skeleton, so that they are high in chemical and thermal stability. Since there exist a distribution for mobility of electrons in the central conjugated systems and that for local mobility, said tetraazaporphyrin derivatives show a large nonlinear optical effect.

What is claimed is:

1. A nonlinear optical element comprising a pair of transparent support members and a tetraazaporphyrin compound located between said support members, said compound being represented by the formula (I):

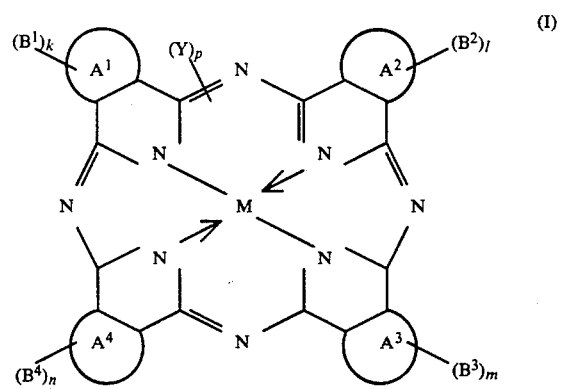

wherein M represents any of the metals of Groups Ia, Ib, IIa, IIb, IIIa, IVa, IVb, Va, Vb, VIa, VIb, VIIa and VIII in the Periodic Table, Si and Ge; Y represents a monovalent organic group having 3 to 20 carbon atoms and selected from the group consisting of alkyl, aryl, aralkyl ester, alkoxyl, aryloxy, trialkylsiloxyl, triarylsiloxyl, triaryloxysiloxy, acyloxyl, alkylthio, arylthio, alkylsulfonyl, arylsulfonyl, carbamoyl and nitrile groups, hydroxyl groups and halogen atoms which can be bonded to M; p represents an integer from 0 to 2, and when p is 2, Y's may be the same or different from each other; $A^1$, $A^2$, $A^3$ and $A^4$ each represents any of the following groups:

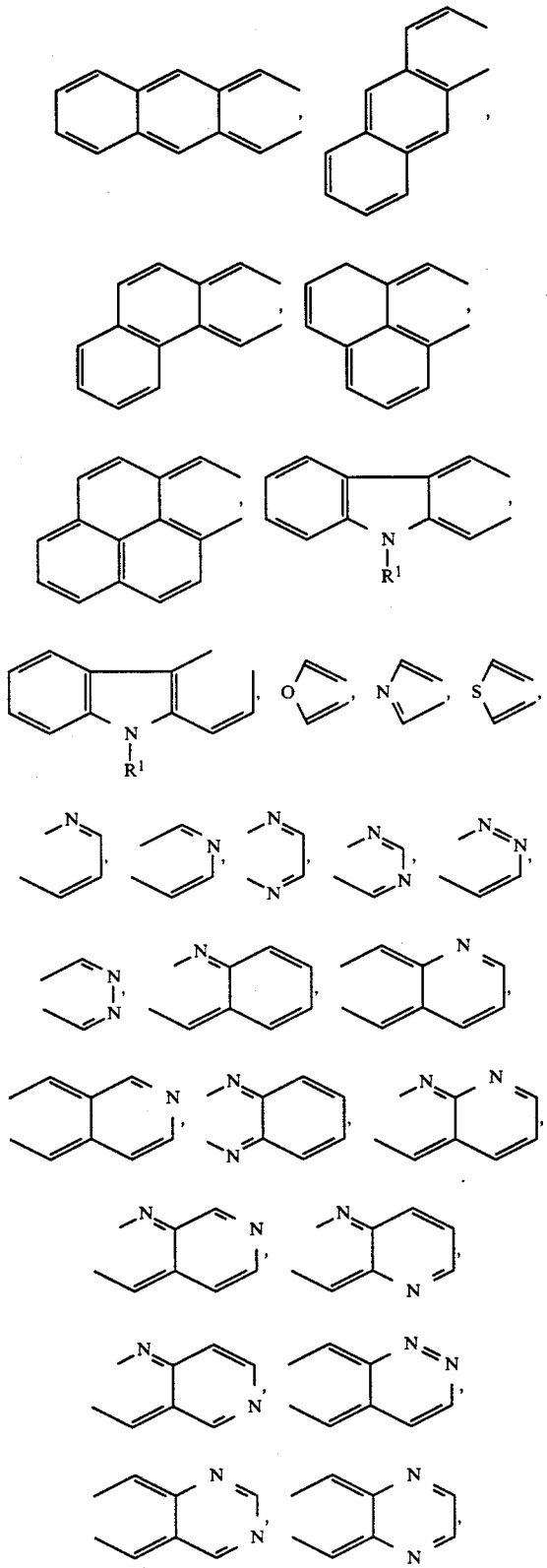

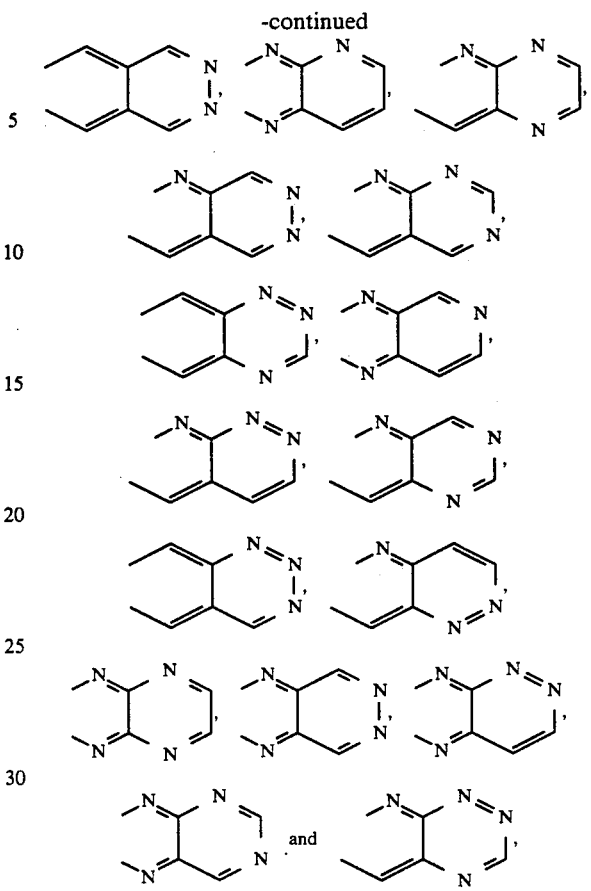

wherein $R^1$ represents a saturated alkyl group of 1 to 10 carbon atoms; $B^1$, $B^2$, $B^3$ and $B^4$ represent same or different groups selected from said monovalent organic groups, same or different halogen atoms, or hydrogen atoms, but all of $B^1$, $B^2$, $B^3$ and $B^4$ cannot be hydrogen atoms at the same time; and k, l, m and n represent independently an integer from 0 to 4, but $k+l+m+n \geq 1$.

2. A nonlinear optical element according to claim 1, wherein Y in the formula (I) is aryloxy group, alkoxy group, trialkylsiloxyl group, triarylsiloxyl group, trialkoxysiloxy group, triaryloxysiloxy group, trityloxyl group, acyloxyl group, alkyl group, aryl group or hydroxyl group.

3. A nonlinear optical element according to claim 1, wherein M in the formula (I) is Si, Ge, Sn, Cu, V, Ti or Cr.

4. A nonlinear optical element according to claim 1, wherein the organic groups $B^1$, $B^2$, $B^3$ and $B^4$ bonded to the aromatic rings represented by $A^1$, $A^2$, $A^3$ and $A^4$ in the formula (I) are at least one group selected from the group consisting of the following substituents; $-R^2$, $-OR^3$, $-SiR^4R^5R^6$, $-SO_2NR^7R^8$, $-CO.R^9$, $-COOR^{10}$, $-O.COR^{11}$, $-CO.NHR^{12}$, $-NR^{13}R^{14}$, $-SR^{15}$, $-SO_2R^{16}$ and $-X^1$ wherein $R^1$ represents an alkyl group having 1-3 carbon atoms; $R^2$ to $R^{16}$ represent a hydrogen atom, an alkyl group having 3 to 20 carbon atoms or an aryl group having 6 to 20 carbon atoms; and $X^1$ represents a halogen atom.

5. A nonlinear optical element according to claim 1, 2, 3 or 4 wherein $A^1$, $A^2$, $A^3$ and $A^4$ in the formula (I) are identical with each other.

6. A nonlinear optical element according to claim 1, wherein in the formula (I) $A^1$, $A^2$, $A^3$ and $A^4$ are identical with each other, and k, l, m and n are also identical with each other.

* * * * *